US006271268B1

(12) United States Patent
Mayne

(10) Patent No.: US 6,271,268 B1
(45) Date of Patent: *Aug. 7, 2001

(54) COMPOSITIONS AND METHODS FOR DECREASING SEBUM PRODUCTION

(75) Inventor: James T. Mayne, Deep River, CT (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/536,480

(22) Filed: Mar. 27, 2000

Related U.S. Application Data

(63) Continuation of application No. 08/298,735, filed on Aug. 31, 1994, now Pat. No. 6,133,326.

(51) Int. Cl.$^7$ .................................................. A61K 7/48
(52) U.S. Cl. ...................... 514/859; 514/864; 424/78.02
(58) Field of Search ........................... 514/859; 424/78.02

(56) References Cited

U.S. PATENT DOCUMENTS

| | | | |
|---|---|---|---|
| 4,302,456 | 11/1981 | Voorhees et al. | 424/251 |
| 4,514,385 | 4/1985 | Damani et al. | 424/81 |
| 4,716,175 | 12/1987 | Hoefle et al. | 514/357 |
| 4,994,465 | 2/1991 | Trivedi | 514/256 |
| 5,204,093 | 4/1993 | Victor | 424/73 |
| 5,834,480 | * 11/1998 | Elkhoury | 514/859 |
| 5,902,805 | * 5/1999 | Breton et al. | 514/859 |
| 5,965,553 | * 10/1999 | Bell et al. | 514/211 |
| 5,994,330 | * 11/1999 | El-Khoury | 514/859 |

FOREIGN PATENT DOCUMENTS

| | | |
|---|---|---|
| 9315058 | 8/1993 | (WO) . |
| 9324458 | 12/1993 | (WO) . |

OTHER PUBLICATIONS

Reindel et al., 1994, Sep.–Oct. Toxicologic Pathology 22(5):510–518, "Toxicologic effects of a novel acyl–CoA: cholesterol acyltransferase inhibitor in cynomolgus monkeys", including corresponding abstract from PubMed (NCBI).

* cited by examiner

Primary Examiner—Peter F. Kulkosky
(74) Attorney, Agent, or Firm—Peter C. Richardson; Paul H. Ginsburg; Alan L. Koller

(57) ABSTRACT

A method of treating diseases caused by sebaceous gland disorders, in humans and animals, which comprises administering to said humans and animals a composition comprising a sebaceous gland secretion inhibiting amount of an active compound comprising an acyl coA cholesterol acyl transferase (ACAT) inhibitor or prodrug therefor.

A composition for use in treating diseases caused by sebaceous gland disorders such as acne in humans and animals which comprises a sebaceous gland secretion inhibiting amount of an acyl coA cholesterol acyl tanferase (ACAT) inhibitor or prodrug therefor and, optionally, a pharmaceutically acceptable carrier.

21 Claims, No Drawings

COMPOSITIONS AND METHODS FOR DECREASING SEBUM PRODUCTION

This application is a continuation of application Ser. No. 08/298,735, filed Aug. 31, 1994 now U.S. Pat. No. 6,133,326.

BACKGROUND OF THE INVENTION

This invention relates to a method of treating diseases caused by sebaceous gland disorders, especially acne, in humans and animals by inhibiting the secretions of such glands by use of acyl coA cholesterol acyl transferase (hereafter 'ACAT') inhibitors or prodrugs therefor (wherein the ACAT inhibitors and prodrugs are referred to hereafter as "active compounds").

Acne is a group of dermatological disorders which are associated with a variety of etiologies. The group of acnes includes chloroacne, ciliaris, cystic, keratosa and vulgaris. In its vulgaris form, it occurs primarily in the face and trunk areas, affecting the appearance of the patient. It probably causes more mental pain and anguish to those afflicted than many other diseases which, from a physical standpoint, may be much more severe. The basic lesion common to the family of diseases referred to as acnes is the comedo or "blackhead" of a pilosebaceous follicle. The condition may be mild and transient with only a few blackheads which can readily be ejected by pressure and are of little concern, or may be severe, persistent, and very disfiguring with the more serious cases causing cystic lesions and frequently leaving permanent scarring.

What appears to occur in the development of acnes is an initial filling up of the follicle with a viscous, keratinous material. This impaction of horny material is the whitehead and blackhead. As a result of bacterial growth in these horny impactions, the follicle ruptures initiating the inflammatory phase of the disease which takes the form of pustules, papules, cysts and nodules.

One of the commonly used methods for acne treatment is the use of "peeling", i.e., as astringent, agents for mild cases which cause exfoliation with the removal of some of the keratinous plugs. In the more serious cases where pustular or cystic lesions exists, the same are evacuated by incision and the contents expressed. Various other therapies have been employed, such as vaccine therapy, to assist in the control of chronic infection and increase the patient's resistance to Staphylococci; cortisone-type steroids; hormone therapy which is applicable only for female patients who may be put on routine contraceptive regimen with estrogens; antibacterial therapy for the treatment of extensive pustular or cystic acne where the patient may be treated with tetracyclines, penicillin, erythromycin, or other of the antibacterial agents, and, in come instances, general surgical skin planing may be used.

Although many different approaches have been used for the treatment of this almost universal affliction, none of the common topical treatments has been found to be particularly effective. Systematic administration of hormones and anti-bacterials has been shown to have some therapeutic merit but may be unacceptable for chronic therapy.

The administration of large oral doses of vitamin A has been suggested as being beneficial in acne, Straumford, J. V.: "Vitamin A: Its Effects on Acne", *Northwest Med.,* 42, 219–225 (August 1943), although other investigators have felt it to be ineffective (Anderson, J. A. D. et al., "Vitamin A in Acne Vulgaris" *Brit. Med. J.,* 2, 294–296 (August 1963); Lynch, F. W. et al., "Acne Vulgaris Treated with Vitamin A" *Arch Derm.,* 55, 355, 357 (March 1947) and Mitchell, G. H. et al., "Results of Treatment of Acne Vulgaris by Intramuscular Injections of Vitamin A" *Arch. Derm.,* 64, 428–430 (October 1951).

Vitamin A acid has been applied topically (Beer, Von P., "Untersuchungen ber die Wirkung Vitamin A-Saure" *Dermatologica,* 124, 192–195 (March 1962) and Stuttgen, G., "Zur Lokalbehandlung von Keratosen mit Vitamin A-Saure" *Dermatologica,* 124, 65–80 (February 1962)) achieving good results in those hyperkeratotic disorders which are responsive to high oral doses of vitamin A. Among those treated by Beer and Stuttgen were patients with acne; however, these investigators reported no effective results on this disorder.

The treatment of acnes with isotretinoin and etretinate is described by J. A. Goldstein, et al. "Comparative effect of isotretinoin and etretinate on acne and sebaceous gland secretion." *J. Am Acad Dermatol,* 6, 760–765 (1982). S. S. Shapiro et al. discuss treatment of acnes with various potential therapeutic entities in "Evaluation of Potential Therapeutic Entities for the Treatment of Acne" *Pharmacology of Retinoids in the Skin. Pharmacol. Skin,* Reichert and Shroot, eds, Karger, Basel, vol. 3, pp 104–22 (1989)).

Lambert, R. W., and Smith, R. E. have discussed the "[e]ffects of 13-cis-retinoic acid on the hamster Meibomian gland", *J. Invest Derm,* 93(2), 321–325 (1989) whereas the effects of retinoids on psoriasis is discussed by Lowe, N. J., and David M. in "Systemic Retinoids in Psoriasis: Comparative Efficacy and Toxicity", *Pharmacology of Retinoids in the Skin. Pharmacol. Skin,* vol. 3, pp 104–122, Reichert and Shroot eds. Karger, Basel, (1989).

U.S. Pat. No. 3,729,568 refers to the use of vitamin A acid (retinoic acid or tretinoin) in the treatment of acne vulgaris.

Co-pending International Patent Application PCT/US92/06485 teaches the use of vitamin A acid derivatives in the treatment of skin diseases including acne.

U.S. Pat. No. 4,703,110 describes the use of para substituted benzoic acid derivatives in the treatment of dermatological disorders including cystic acne.

U.S. Pat. No. 4,927,928 teaches the use of benzamido compounds in the treatment of dermatological diseases having an inflammatory and/or immunoallergic component, including acne vulgaris, senile acne and medicinal or professional acne.

SUMMARY OF THE INVENTION

This invention provides a method for pharmacologically treating diseases (hereafter "diseases") caused by sebaceous gland disorders, such as acnes, in humans and animals, which comprises administering to said humans and animals a composition comprising a sebaceous gland secretion inhibiting amount of an acyl coA cholesterol acyl transferase (ACAT) inhibitor or prodrug therefor (hereafter referred to as "active compound").

According to another aspect of the invention there is provided a method, as described above, wherein said composition comprises an admixture of said sebaceous gland secretion inhibiting amount of the active compound and a pharmaceutically acceptable carrier.

Yet another aspect of the invention provides a method for pharmacologically treating the above-indicated diseases by orally administering an amount of the active compound effective for treating the disease.

Another aspect of the invention provides a method, as described above, wherein the active compound is administered in an admixture with a pharmaceutically acceptable carrier.

According to another aspect of the invention there is provided a method, as described above, wherein the pharmaceutically acceptable carrier is a solvent for the active compound.

Yet another aspect of the invention provides a method, as described above, wherein the pharmaceutically acceptable carrier comprises a non-solvent for the active compound.

According to another aspect of the invention there is provided a method for pharmacologically treating the above-indicated diseases by topically administering a disease treating effective amount of the active compound.

Another aspect of the invention provides a method, as described above, wherein the active compound is administered as a composition further comprising a pharmaceutically acceptable carrier.

Yet another aspect of the invention provides a method, as described above, wherein said composition comprises a gel, cream, lotion or topical solution.

According to another aspect of the invention there is provided a composition for treating diseases, caused by sebaceous gland disorders, such as acnes, in humans and animals, which comprises a sebaceous gland secretion inhibiting amount of an active compound.

Yet another aspect of the invention provides a composition, as described above, further comprising a lower alkanol having from one to four carbons; water; a gel-forming amount of carboxyvinyl polymer; one or more polyhydric alcohols selected from the group consisting of a lower alkylene glycol having from two to six carbons, glycerine and polyethylene glycol having an average molecular weight from 200 to 2000, said composition having a pH range of from about 6.5 to about 9.0.

Also encompassed by this invention is a composition, as described above, which further contains an effective amount of a film-forming agent such as carboxymethyl cellulose, hydroxyethyl cellulose, poly(vinylpyrrolidinone) and mixtures thereof.

DETAILED DESCRIPTION OF THE INVENTION

This invention relates to a method for treating diseases caused by sebaceous gland disorders, especially acne, in humans and animals by inhibiting the secretions of such glands by administering to said humans and animals a sebaceous gland secretion inhibiting amount of an acyl coA cholesterol acyl transferase (hereafter 'ACAT') inhibitors or prodrugs therefor. The ACAT inhibitors and their prodrugs will hereafter be referred to as "active compounds".

ACAT inhibitors useful in the practice of the invention, and their preparation are disclosed, inter alia, in co-pending U.S. patent application Ser. Nos. 08/251075 and 08/133,206 and International Patent Application Numbers PCT/US92/10886 and PCT/US93/03539 (all of which are assigned to the assignee of this application and incorporated herein by reference). Other ACAT inhibitors, useful in the practice of the invention, are referred to in, e.g., U.S. Pat. Nos. 4,994,465, 4,716,175 (the '175 patent) and 4,743,605 (a divisional of the '175 patent) and in the European Patent Applications having publication numbers 0 242 610, 0 245 687, 0 252 524, 0 293 880, 0 297 610, 0 335 374, 0 335 375, 0 386 487, 0 399 422, 0 415 123, 0 421 456 and 0 439 059. Additional ACAT inhibitors are described in PCT publications WO 90/15048 and WO 91/04027.

Most preferred ACAT inhibitors for use in the invention are selected from (2S) N-(2,4-bis(methylthio)-6-pyrid-3-yl)-(2-hexylthio)decanoamide, (Compound I) the preparation of which is described in co-pending U.S. patent application Ser. No. 08/251,075, incorporated herein by reference;

N-(2,6-Diisopropylphenyl)-N'-[2-(naphth-2-yl)-6,6,6-trifluorohexyl]urea (Compound II);

N-[(2,4-bis(ethylthio)-6-methylpyridin-3-yl]-N'-heptyl-N'-(4-isopropylbenzyl)urea (Compound III; and N-[(2,4-bis(ethylthio)-6-methylpyridin-3-yl]-N'-heptyl-N'-(4-propylbenzyl)urea (Compound IV); and N-[(2,4-bis(ethylthio)-6-methylpyridin-3-yl]-N'-[2-(2,5-dimethylphenyl)-6-phenylhexyl]urea (Compound V) the preparations of which are described in co-pending International Patent Application Number PCT/US93/03539, incorporated herein by reference.

Inhibition of acyl-CoA cholesterol acyl transferase (ACAT) blocks the esterification of free cholesterol to cholesteryl esters. Cholesterol esters are the primary transportation and storage forms of cholesterol in animals. In the intestines, ACAT inhibitors have been shown to inhibit the absorption of cholesterol from the gut. In the liver, inhibition of ACAT has been shown to decrease the formation and secretion of cholesterol-containing lipoproteins by decreasing the cholesteryl ester mass of the lipoprotein core. For these reasons, ACAT inhibitors have previously been explored as potential therapy for hypercholesterolemia.

Dermal sebaceous glands are holocrine glands that secrete a mixture of lipids known as sebum. Sebum is composed of triglycerides, wax, sterol esters and squalene. There is considerable variation in the composition of human sebum based on individual variables such as age, sex, diet, and disease. Sebum is produced in the acinar cells of sebaceous glands, accumulates as those cells age and migrates towards the center of the gland. At maturation, the acinar cells lyse and release sebum into the lumenal duct, from which the sebum is secreted.

Formation of sebum is regulated by a variety of hormones that act primarily to regulate the rate of lipid metabolism. Although the exact biochemistry is poorly understood, it is believed that waxes and sterols are converted, within acinar cells, to a stable ester form for storage via the activity of a variety of acyl and fatty acid transferases. These esters are then stored in lipid droplets within the acinar cells prior to release. It is, therefore, reasonable to propose that an inhibitor of ACAT or other transferases, which block esterification, within the acinar cells of sebaceous glands would have the ability to decrease ester formation and thereby decrease overall sebum production. Decreased sebum production has therapeutic benefits in diseases caused by sebaceous gland disorders, such as acnes, characterized by over-production of sebaceous glands. Decreased sebum production as a result of retinoid therapy is a major factor in the successful use of these agents to treat various types of acne.

Although a theory has been proposed for the mechanism of the effect of the ACAT inhibitors on the production of sebum and, therefore, on the treatment of diseases caused by sebaceous gland disorders, the present invention is not dependent upon the validity of that theory.

The active compounds in the compositions of the invention may be administered to a subject, in need of treatment, by a variety of conventional routes of administration, including oral, parenteral and topical. In general, the active compound will be administered orally or parenterally at dosages between about 0.5 and 25 mg/kg body weight of the subject to be treated per day, preferably from about 1.0 to 10 mg/kg. However, some variation in dosage will necessarily occur depending on the condition of the subject being treated. The person responsible for administration will, therefore, determine the appropriate dose for the individual subject.

The active compound may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compound and the pharmaceutically acceptable carriers are then readily administered in a variety of dosage forms such as tablets, powders, lozenges, syrups, topical and injectable solutions, gels, creams lotions and the like.

These pharmaceutical compositions can, if desired, contain additional excipients such as flavorings, binders, and the like. Thus, for purposes of oral administration, tablets containing ingredients such as sodium citrate, calcium carbonate and calcium phosphate may be employed along with disintegrants such as starch, alginic acid and certain complex silicates, together with binding agents such as polyvinylpyrrolidone, sucrose, gelatine and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred fillers include lactose, or milk sugar, and high molecular weight polyethylene glycols. When aqueous suspensions or elixirs are desired for oral administration, the active ingredient therein may be combined with sweetening or flavoring agents, coloring matter and, if desired, emulsifying or suspending agents, together with diluents such as water, ethanol, propylene glycol, glycerine and combinations thereof.

For parenteral administration, solutions of the active compound in sesame or peanut oil, aqueous propylene glycol, or sterile aqueous solution may be employed. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques.

For topical administration a gel-forming composition, such as a carboxyvinyl polymers, or mixtures of gel-forming compositions are used in combination with the active compounds of the invention. Commercially available carboxyvinyl polymers are include Carbopol (trademark) 934, 940 and 941 (from Goodrich Chemicals, U.S.A.).

An aqueous solution containing the carboxyvinyl polymer is acidic, since the polymer has free carboxylic acid residues. Neutralization of the aqueous solution with an appropriate base furnishes a viscous gel with desired viscosity. The appropriate bases which can be used are alkanolamines, such as monoalkanolamines having from one to four carbon atoms including methanolamine, ethanolamine, propanolamine and butanolamine; dialkanolamines having from two to eight carbon atoms, e.g., dimethanolamine, diethanolamine, dipropanolamine and dibutanolamine; and trialkanolamines, having from three to twelve carbon atoms, for instance, trimethanolamine, triethanolamine, tripropanolamine and tributanolamine. Other bases, useful in the practice of the invention, include inorganic bases such as sodium hydroxide, potassium hydroxide and potassium carbonate and organic bases such as alkylamine, dialkylamine and trialkylamine. A preferred amount of the gel-forming agent is from about 0.2% to about 2.0% by weight of the total.

A gel ointment formulation containing carboxyvinyl polymer is generally stable. It has a constant viscosity with very little variation due to temperature or time. However, several problems may arise when the compositions of this invention containing carboxyvinyl polymers are applied to the skin. It may sometimes happen that the polymer is salted out by the salt contained in sweat and forms soft agglomerates which disintegrate easily. In such a case, the active ingredient may be lost before it is absorbed through skin and the formulation affords an unpleasant feeling on administration.

Accordingly, the formulation must be administered after the area of application is freed of sweat and cleaned. It has been discovered that if certain hydrophilic polymers are incorporated in the formulation, the ointment can be administered topically even on the sweating skin to form a suitable film without the above problems. Hydrophilic polymers useful in connection with this invention include poly (vinylpyrrolidinone), carboxymethyl cellulose, hydoxyethyl cellulose and mixtures thereof. A preferred amount of the film-forming agents is from about 0.2% to about 2.0% by weight of the total formulation.

In addition to the above-mentioned film-forming agents, various other ingredients can be incorporated into the compositions of this invention to improve their therapeutic efficacy and stability. These include antiseptics such as benzyl alcohol, corneous tissue-dissolving agents such as urea and suitable skin-permeation enhancing adjuvants, like diethyl sebecate, etc., which are well-known to those skilled in the art.

The compositions of this invention have a pH range of from about 6.5 to about 9.0, and preferably from 6.5 to 8.0. In general, it is believed that the percutaneous absorption or skin-penetration of a given drug is dependent upon the ratio of lipophilicity to water solubility (partition coefficient) and that a high ratio is preferred, but too high a ratio adversely decreases the absorption and skin-penetration. A preferred pH range for the compositions of this invention is from about 6.5 to about 8.0.

The following excipients may be used in preparing gels for use in accordance with the invention; lower alkanols, for example, methanol, ethanol, isopropanol and butanol; and lower alkylene glycols having from two to six carbons which can be used includes ethylene glycol, propylene glycol and butylene glycol. Glycerine or polyethylene glycol having an average molecular weight of from 200 to 2000 can also be used in place of glycol. It is possible to use only one kind of such polyhydric alcohol, but more than one kind may also be used. A preferred amount of the lower alkanol comprises from about 10% to about 50%, water from about 30% to about 60% and the polyhydric alcohol from about 5% to about 40% by weight of the total composition.

The following are typical formulations for use in connection with the invention wherein the ACAT inhibitor is N-(2,6-diisopropylphenyl)-N'-[2-(naphth-2-yl)-6,6,6-trifluorohexyl]urea (Compound I) which was prepared according to Example 242 of (U.S. patent application Ser. No. 08/251,075, incorporated herein by reference.

Formulation 1—Oral Tablet

An oral tablet was prepared having the following formula:

| Ingredient | Mg Per Tablet |
|---|---|
| ACAT inhibitor | 100.0 |
| Lactose | 122.0 |
| Microcrystalline Cellulose | 60.0 |
| Sodium starch glycollate | 15.0 |
| Magnesium stearate | 3.0 |

The ingredients were blended and compressed into tablets.

Formulation 2—Oral Solution

An oral solution was prepared having the following formula:

| Ingredient | Percent by Weight |
|---|---|
| ACAT inhibitor | 2.0 |
| Ethyl alcohol | 10.0 |
| Benzyl alcohol | 1.0 |
| Peppermint Flavor | 0.2 |
| Vanillin | 0.2 |
| Polysorbate 40 | 0.1 |
| Sucrose | 50.0 |
| Purified water | balance |

The ingredients were combined and mixed to form a uniform solution.

Formulation 3—Topical Gel

A gel was prepared having the following composition:

| Ingredient | Percent by Weight |
|---|---|
| ACAT inhibitor | 0.50 |
| Propylene glycol | 20.00 |
| Ethanol | 20.00 |
| Carboxyvinyl polymer [Carbomer 940 (trademark)] | 1.00 |
| Hydroxyethyl cellulose | 0.40 |
| Benzyl alcohol | 1.00 |
| Sodium hydroxide 1N | to pH 6 |
| Distilled water | balance |

The components other than sodium hydroxide were combined to yield a homogeneous dispersion. Addition of sodium hydroxide caused the mixture to gel yielding a ready-to-use semisolid.

Formulation 4—Topical Cream

A cream was prepared consisting of:

| Ingredient | Percent by Weight |
|---|---|
| ACAT inhibitor | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |
| Methylparaben | 0.25 |
| Disodium edetate | 0.05 |
| Distilled water | balance |

The first four ingredients were heated to approximately 70° C. to produce a uniform melt. The remaining ingredients were combined, heated to approximately 75° C., and added, with mixing, to the previously prepared melt. The emulsion, thus formed, was subsequently homogenized and cooled to yield a smooth white cream.

Formulation 5—Topical Lotion

A lotion was prepared having the following composition:

| Ingredient | Percent by Weight |
|---|---|
| ACAT inhibitor | 0.50 |
| Glyceryl monostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | balance |

The first four ingredients were combined and heated to approximately 70° C., then added with agitation to a mixture of the remaining ingredients, also at about 70° C. The emulsion was appropriately homogenized and cooled to produce a smooth, white, pourable lotion.

Formulation 6—Topical Solution

A topical solution was prepared having the following composition:

| Ingredient | Percent by Weight |
|---|---|
| ACAT inhibitor | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | balance |

All ingredients except sodium hydroxide were combined with agitation, and the pH of the resultant solution was adjusted with 1 N sodium hydroxide, to pH 6, to yield a free-flowing, quick-drying topical solution.

The above Formulations were repeated wherein the Compound I was replaced by Compounds II through V the preparations of which are described in the aforementioned co-pending International Patent Application Number PCT/US93/03539.

The topical formulations presented herein are examples of typical gel, cream, lotion, or solution dosage forms, of active compounds, for use in the treatment of diseases caused by sebaceous gland disorders. Other optional components can be added, or excipient ratios can be adjusted, to enhance cosmetic acceptability of the formulations. Additionally, these alterations can be made to customize the composition toward a particular active compound, for example to ensure solubilization or to enhance chemical or physical stability. Optional components would include viscosity adjusters such as celluloses; emollient oils such as mineral oil or glycerides; humectants such as polyols; cosolvents such as isopropyl alcohol or acetone; emulsifying agents of the anionic, cationic and nonionic types; preservatives; antioxidants; opacifiers; colorants and perfumes.

The ability of the active compounds to inhibit sebaceous gland secretions is determined by visual microscopic inspection of the atrophication of dermal glands and further demonstrated in the following Examples. Additional evidence is presented demonstrating functional changes in sebaceous glands via the following ophthalmological techniques which are performed with the aid of a slit-lamp biomicroscope:

Schirmer Tear Tests

Standardized strips of filter paper were partially inserted into the ventral conjunctival sac perpendicular to the lid margin; capillary action draws fluid along the strip. The length wetted after one minute was measured, permitting evaluation of the rate of production of the lipid phase of the tear film by the lacrimal glands.

Tear film breakup time (BUT)

Fluorescein dye was instilled into the conjunctival sac and allowed to mix with the tear film. The lids were manually retracted and the time measured to the first observed disruption of the homogeneous dye film on the cornea. The dye distributes into the outer, lipid layer of the tear film. Changes in the time to disruption are interpreted as evidence of tear film instability.

EXAMPLE 1

A group of 3 male and 3 female Beagle dogs was given Compound I twice daily by oral gavage at a dose of 25 mg/kg (50 mg/kg/day) for 14 days. The drug was administered as a suspension in olive oil. The volume of the administered dose was 2 ml/kg at a concentration of 12.5 mg/ml. A similar group was dosed with olive oil twice daily and served as a vehicle control. Following the dosing phase of the study, the study continued into a reversibility phase of up to 73 days.

Ophthalmoscopic examinations, including a standard examination (direct and indirect ophthalmoscopy), Schirmer tear test and tear film breakup time (BUT) were performed by a clinical veterinarian once prior to administration of the active compound and then, after administration of the active compound, on days 13, and 15 (Schirmer tear test), 51, 72 and 105. To facilitate the routine eye examination, mydriasis was induced by 1.0% tropicamide (Mydriacycl®, Alcon Laboratories). were used for assessment of the precorneal tear film:

Representative animals from the treated group were sent to pathology for necropsy on days 15, 55 (day 41 of the reversibility phase), and 87 (day 73 of the reversibility phase). Eyelid and skin samples were collected and processed in 10% neutral buffered formalin.

Results

Excessive lacrimation was first observed in most animals by day 7. At that time eye examinations revealed no apparent gross changes. The only consistent treatment effects detected by the clinical/functional tear film tests was an increase in the Tear Film Breakup Time of treated animals.

Microscopic examination of tissues revealed almost complete atrophy of the acinar (sebaceous) components of the eyelid sebaceous (Meibomian) glands with dilation of the central collecting duct and some chronic inflammatory infiltrates in two of the animals necropsied on day 15. The dermal sebaceous glands were also completely atrophic and lacked their normal acinar architecture. In the animal necropsied on day 55, the dermal sebaceous glands appeared normal, indicating complete reversal of the atrophic effects of Compound I after 41 days off drug. In the Meibomian glands of this animal, a majority of the sebaceous acini appeared normal, but dilated collecting ducts and some residual chronic inflammation were still apparent in some glands. In the animal necropsied on day 87 (day 73 of reversal), the dermal sebaceous glands appeared normal as did the majority of the eyelid (Meibomian) glands. However, with close scrutiny, some residual effects in the form of moderately dilated collecting ducts were observed in an occasional eyelid gland from this animal.

It may be concluded from the above observations that sebaceous gland atrophy associated with the administration of Compound I to the dog is reversible. However, the time required for complete reversal is considerable, and reversal appears to take longer in the eyelid than in the dermal sebaceous glands.

EXAMPLE 2

Groups of male and female Beagle dogs were given Compound I twice daily by oral gavage at doses of 0.1 mg/kg/day (0.05 mg/kg b.i.d., 3/sex*), 1.0 mg/kg/day (0.5 mg/kg b.i.d., 3/sex), or 10 mg/kg/day (5 mg/kg b.i.d., 4/sex). The drug was administered as a suspension in a 0.5% aqueous methylcellulose vehicle. A similar group (3/sex) was dosed with the methylcellulose vehicle alone and served as a vehicle control. Animals were dosed for one month or until the first clinical evidence of sebaceous gland dysfunction (lacrimation/epiphora, alopecia) was observed. At 24 hours after the observation of such signs, drug administration was terminated in affected animals and they were maintained without drug treatment (reversal phase) until clinical signs had abated. Once clinical reversal was documented for affected animals, they were necropsied. Based on these criteria, high dose animals were entered into the reversal phase and were monitored in the absence of drug for 13 to 18 days.

*n/sex=number of animals of each sex, i.e., 3 males and three females

A series of ophthalmoscopic examinations were performed by a clinical veterinarian, i.e., once prior to treatment initiation and then on days 9, 11, 24–26 and 46. Ophthalmic examinations included a routine ophthalmic examination, Schirmer Tear test and tear film breakup time (BUT). An additional series of ophthalmic examinations were performed on any animal exhibiting signs of lacrimal dysfunction.

Skin Biopsy Collection Procedure

Punch skin biopsies were collected from all dogs prestudy and at the end of the study. An additional skin biopsy was collected from affected dogs at the beginning of the reversal period.

The skin along the dorsal midline and roughly between the scapulae was gently clipped free of hair and a local anesthetic (Udocaine [trademark]) was injected subcutaneously at the proposed biopsy site. The skin was gently cleansed and covered with a sterile drape. The biopsy specimen was cut with a sterile biopsy punch (about 6 mm diam.) and placed in 10% buffered formalin fixative. The resulting skin wound was closed with a surgical skin stapler and the site was monitored closely.

Results

Lacrimation became evident at the high dose on day 6 and persisted throughout the study. A single intermediate dose animal exhibited signs of lacrimation on day 22.

Sebaceous gland atrophy was apparent microscopically in a variety of regions of the skin (see table below). Cells in affected glands had a reduced amount of cytoplasm and contained large, clear vacuoles rather than the many small vacuoles seen in normal gland cells. Acini of affected glands were smaller than normal, and ducts were often dilated and filled with eosinophilic debris, most likely keratin and degenerate cells. Some glands also contained a low grade influx of chronic inflammatory cells. In those animals allowed to undergo a period of reversal, dermal glands had returned to a normal morphologic appearance by 13–18 days off drug. Minimal dilation of ducts remained in the eyelid (Meibomian) sebaceous glands of two animals (#19 and 23) at the end of reversal.

Grade of Sebaceous Gland Atrophy in Affected Animals[a]

| Animal Number[b] | Inguinal (Skin Section) | Eyelid (Meibomian Gland) | Perianal Gland | Biopsy (Predose) | Biopsy (Start of Reverse) | Biopsy (Day of Necropsy) |
|---|---|---|---|---|---|---|
| 17 | N | N | N | N | N | N |
| 19[R] | N | 1 | N | N | 3 | N |
| 20 | 3 | 3 | 3 | N | n/a | 3 |
| 21 | 3 | 3 | 3 | N | n/a | 3 |
| 22* | n/a | 4 | 4 | N | n/a | n/a |
| 23[R] | N | 1 | N | N | 3 | N |
| 24 | 4 | 3 | 3 | N | n/a | n/a |
| 25* | n/a | 3 | 4 | N | n/a | 2 |
| 26[R] | N | N | N | N | 3 | N |

[a]Subjective grade of sebaceous gland atrophy (1 = minimal; 5 = severe) noted in skin samples from various locations (N = unremarkable; n/a = not applicable). All skin samples were graded "unremarkable" for any animal not listed.
[b]#17 = intermediate dose female, #19–22 = high dose males, #23–26 = high dose females
[R]Reversal dogs
*animal #'s 22 and 25 necropsied in moribund condition on days 7 and 10, respectively, due to adrenal insufficiency.

Sebaceous gland atrophy, similar to the above, was also reported in connection wih the investigation of this compound in Example 1. It was found that all sebaceous glands, including the Meibomian glands of the eyelid, tended to be similarly affected by the compound. The punch skin biopsies contained a number of sebaceous glands, each, and were adequate for determining the presence or absence of sebaceous gland atrophy. This study demonstrated that the sebaceous gland lesion is dose-dependent and reversible in dogs when the drug is removed immediately after the onset of clinical signs.

EXAMPLE 3

Male Hartley Crl:(HA)BR guinea pigs, were randomly assigned to five dose groups (8 males/group). Four of the groups received Compound I (20 mg/kg), Compound II (40 mg/kg), Compound III (35 mg/kg) or Compound IV (51 mg/kg), administered daily for 5 days by oral gavage, in a liquid hamster diet vehicle. The fifth group received an equivalent volume of liquid hamster diet daily and served as a vehicle control.

Samples of interscapular skin and eyelid were also collected and processed for microscopic examination of sebaceous glands.

Results

Treatment-related clinical observations were limited to lacrimation observed on days 3 and 5 in two to six of the eight animals in each treated group. Previous evidence collected in dogs has established that lacrimation produced by ACAT inhibitors is symptomatic of eyelid sebaceous gland (Meibomian gland) atrophy and dysfunction.

There were no discernible changes in the sebaceous glands of the interscapular skin samples. However, in eyelid sebaceous glands, cleft-like degenerative changes were noted in animals from all drug-treated groups.

EXAMPLE 4

Male and female beagle dogs were assigned to two treated groups and a vehicle control group (2/sex/group). Treated animals received either Compound V or Compound I orally at doses of 300 (150 mg/kg b.i.d.) or 5 (2.5 mg/kg b.i.d.) mg/kg/day, respectively, for 5 days. Control animals received an equivalent volume of the vehicle, 0.5% aqueous methylcellulose, twice daily.

On day 36, all treated animals were sent to Pathology for necropsy. The anal glands and a sample of interscapular skin were placed in fixative.

Results

Lacrimation became apparent in the treated animals during the dosing phase of the study and persisted throughout a portion of the reversibility phase.

Histopathology observations revealed that there were no significant changes in the perianal and interscapular skin samples of two animals treated with Compound V and four animals treated with Compound I. The interscapular skin samples of one animal treated with Compound V had fewer and smaller sebaceous glands which was indicative of mild atrophy. The perianal sections of skin of this dog were comparable to control dogs.

The invention has been illustrated by several Examples. It is obvious that many changes and modifications may be made thereto without departing from the spirit or scope of the invention which is defined by the claims.

What is claimed is:

1. A method of treating a sebaceous gland disorder in a human or animal in need of said treatment, which comprises administering to said human or animal a composition comprising a sebaceous gland secretion inhibiting amount of an acyl coA cholesterol acyl transferase (ACAT) inhibitor or prodrug therefor.

2. The method of claim 1 wherein said disorder is manifested as acne.

3. The method of claim 1 wherein said composition is administered orally.

4. The method of claim 3 wherein said composition comprises an admixture of said active compound and a pharmaceutically acceptable carrier.

5. The method of claim 4 wherein said pharmaceutically acceptable carrier comprises a solvent for the active compound.

6. The method of claim 1 wherein said composition is administered topically.

7. The method of claim 6 wherein said composition is selected from the group consisting of gels, creams, lotions and topical solutions.

8. The method of claim 7 wherein said composition is a gel ointment comprising in an aqueous system a sebaceous gland secretion inhibiting amount of the active compound, from about 10% to about 50% by weight of a lower alkanol having from one to four carbon atoms; from about 0.2% to about 2.0% by weight of carboxyvinyl polymer; from about 5% to about 40% by weight of at least one polyhydric alcohol selected from the group consisting of lower alkylene glycol having from two to six carbon atoms, glycerine and polyethylene glycol having an average molecular weight of 200 to 2,000; and from about 1.0% to about 3.0% by weight of at least one alkanolamine having from one to four carbon atoms, dialkanolamine having from two to eight carbon atoms and trialkanolamine having from three to twelve carbon atoms; and from about 0.2% by weight to about 2.0% by weight of at least one film-forming agent selected rom the group consisting of carboxymethyl cellulose, hydroxyethyl cellulose and polyvinylpyrrolidone, and sufficient water to total 100%, said composition having a pH range of from about 6.5 to about 9.0.

9. The method of claim 1 wherein the active compound is selected from the group consisting of (2S) N-(2,4-bis(methylthio)-6-pyrid-3-yl)-(2-hexylthio)decanoamide;

N-(2,6-Diisopropylphenyl)-N'-[2-(naphth-2-yl)-6,6,6-trifluorohexyl]urea;

N-[(2,4-bis(ethylthio)-6-methylpyridin-3-yl]-N'-heptyl-N'-(4-isopropylbenzyl)urea;

N-[(2,4-bis(ethylthio)-6-methylpyridin-3-yl]-N'-heptyl-N'-(4-propylbenzyl)urea;

N-[(2,4-bis(ethylthio)-6-methylpyridin-3-yl]-N'-[2-(2,5-dimethylphenyl)-6-phenylhexyl]urea; and prodrugs therefor.

10. A composition for use in the treatment of diseases caused by sebaceous gland secretions in humans and animals comprising a sebaceous gland secretion inhibiting amount of an active compound comprising an ACAT inhibitor or prodrug therefor and a tropical carrier.

11. The composition of claim 10 wherein said active compound is selected from the group consisting of (2S) N-(2,4-bis methylthio)-6-pyrid-3-yl)-(2-hexylthio)decanoamide;

N-(2,6-Diisopropylphenyl)-N'-[2-(naphth-2-yl)-6,6,6-trifluorohexyl]urea;

N-[(2,4-bis(ethylthio)-6-methylpyridin-3-yl]-N'-heptyl-N'-(4-isopropylbenzyl)urea;

N-[(2,4-bis(ethylthio)-6-methylpyridin-3-yl]-N'-heptyl-N'-(4-propylbenzyl)urea;

N-[(2,4-bis ethylthio)-6-methylpyridin-3-yl]-N'-[2-(2,5-dimethylphenyl)-6-phenylhexyl]urea; and prodrugs therefor.

12. The composition of claim 10, which is in the form of a gel, cream, lotion or topical solution.

13. The composition of claim 12, comprising a gel ointment, comprising in an aqueous system a sebaceous gland secretion inhibiting amount of an active compound; from about 10% to about 50% by weight of a lower alkanol having from 25 one to four carbon atoms; from about 0.2% to about 2.0% by weight of carboxyvinyl polymer; from about 5% to about 40% by weight of at least one polyhydric alcohol selected from the group consisting of lower alkylene glycol having from two to six carbon atoms, glycerine and polyethylene glycol having an average molecular weight of 200 to 2,000; from about 1.0% to about 3.0% by weight of at least one alkanolamine 30 having from one to four carbon atoms, dialkanolamine having from two to eight carbon atoms and trialkanolamine having from three to twelve carbon atoms; and from about 0.2% by weight to about 2.0% by weight of at least one film-forming agent selected rom the group consisting of carboxymethyl cellulose, hydroxyethyl cellulose and polyvinylpyrrolidone, and sufficient water to total 100%, said composition having a pH range of from about 6.5 to about 9.0.

14. A composition as claimed in claim 13 wherein the active compound is present at a concentration level of from about 0.3% to about 2.0% by weight of the total.

15. A composition as claimed in claim 13 wherein water is present at a concentration level of from about 30% to about 60% by weight of the total.

16. The composition of claim 10 formulated as a gel, cream or lotion.

17. A method of decreasing sebum production in a human or animal in need of such treatment, which comprises administering to said human or animal a composition comprising a sebum production-inhibiting amount of an acyl coA cholesterol acyl transferase (ACAT) inhibitor or prodrug thereof.

18. The method of claim 17, wherein the composition is administered orally.

19. The method of claim 17, wherein the composition is administered topically.

20. The method of claim 19, wherein the composition is formulated as a gel, cream, lotion or topical solution.

21. The method of claim 19, wherein the composition is formulated as a gel, cream or lotion.

* * * * *